United States Patent [19]

Gray et al.

[11] Patent Number: 5,002,692
[45] Date of Patent: Mar. 26, 1991

[54] AMIDE LIQUID CRYSTAL COMPOUNDS: MIXTURES AND DEVICES USING THEM

[75] Inventors: George W. Gray; David Lacey; Kenneth J. Toyne; Richard M. Scrowston, all of North Humberside; Lawrence K. M. Chan, Middlesex; Madeline J. Bradshaw, Near Newent; Victoria Brimmell, Ears Croome, all of England

[73] Assignee: The Secretary of State for Defence in Her Britannic Majesty's Government of the United Kingdom of Great Britain and Northern Ireland, Whitehall, London, England

[21] Appl. No.: 279,461

[22] Filed: Dec. 1, 1988

[30] Foreign Application Priority Data

Apr. 1, 1986 [GB] United Kingdom ............... 8607974

[51] Int. Cl.$^5$ .................. C09K 19/20; C09K 19/12; G02F 1/13
[52] U.S. Cl. ........................ 252/299.65; 252/299.64; 252/299.66; 252/299.67; 350/350 S; 560/41
[58] Field of Search .................... 252/299.64, 299.65, 252/299.66, 299.67; 350/350 S; 560/41

[56] References Cited

U.S. PATENT DOCUMENTS 4,536,060  8/1985  Takamatsu ................. 252/299.2 X
4,764,619  8/1988  Gunjima et al. ........... 252/299.61 X
4,824,217  4/1989  Chan et al. ................. 350/350.5
4,886,620 12/1989  Hopf et al. ................. 252/299.61

OTHER PUBLICATIONS

*Chemical Abstracts,* 9th col., Index (1972–76), p. 955f.

Primary Examiner—Robert L. Stoll
Assistant Examiner—Cynthia Harris
Attorney, Agent, or Firm—Nixon & Vanderhye

[57] ABSTRACT

Amides having the following structure:

$$X-CO-Z^1 \text{\textendash} Y-CO-Z^2 \text{\textendash}_y CHCON \begin{matrix} R \\ | \\ * \end{matrix} \begin{matrix} E \\ \diagdown \\ D \end{matrix}$$

$$R^1 \text{\textendash} \left[ A \right]_a \text{\textendash} A \text{\textendash} \left[ B \right]_b \text{\textendash} B \text{\textendash} \left[ C \right]_c$$

$$\text{\textendash} \left[ F \right]_f \text{\textendash} \left[ G \right]_g$$

used in ferroelectric smectic liquid crystal mixtures, especially as pitch compensators and liquid crystal compositions containing them.

21 Claims, 3 Drawing Sheets

Route A $$\text{HO} \overset{R}{\underset{*}{C}} \text{H COOH}$$

(i)

$$\text{HO} \overset{R}{\underset{*}{C}} \text{H COO CH}_2 \text{\textendash} \bigcirc$$

(ii)

$$R^1 \text{\textendash} \left[ \bigcirc \right]_x \text{\textendash} \text{COO} \overset{R}{\underset{*}{C}} \text{H COO CH}_2 \text{\textendash} \bigcirc$$

(iii)

$$R^1 \text{\textendash} \left[ \bigcirc \right]_x \text{\textendash} \text{COO} \overset{R}{\underset{*}{C}} \text{H COOH}$$

(iv)

$$R^1 \text{\textendash} \left[ \bigcirc \right]_x \text{\textendash} \text{COO} \overset{R}{\underset{*}{C}} \text{H CON} \begin{matrix} E \\ \diagdown \\ D \end{matrix}$$

Route A

Route B

AMIDE LIQUID CRYSTAL COMPOUNDS: MIXTURES AND DEVICES USING THEM

This application is a continuing application under 35 USC 363 of International Application No. PCT/GB87/00223, filed on Apr. 1, 1987, now PCT pub. WO87/05896.

This invention relates to liquid crystal mixtures and to compounds for use in them. The invention is particularly concerned with ferroelectric smectic liquid crystal mixtures and compounds. The invention also relates to electro-optical devices incorporating these mixtures.

Ferroelectric smectic liquid crystal materials utilise the ferroelectric properties of the chiral tilted smectic phase, i.e. the chiral smectic C, F, G, H, I, F and K phases (hereinafter designated $S_c^*$ etc., the asterisk * denoting chirality). The $S_c^*$ phase is most commonly sought for use in electro-optical devices as it is the most fluid, and it is also desirable that the material shows and $S_A$ phase and a nematic (N) phase at temperatures above the $S_c^*$ phase, to assist in surface alignment.

Ferroelectric liquid crystal materials ideally have a low viscosity, a broad smectic liquid crystal temperature range, stability etc., and should show a high spontaneous polarisation coefficient (Ps, measured in $nCcm^{-2}$). Although some single componet materials show these properties, it has become common practice to use a mixture of compounds which together show a chiral tilted smectic phase.

Generally such mixtures include at least one compound which shows a smectic phase without necessarily being chiral ("smectic host"), and at least one optically active compound ("Chiral dopant") the presence of which in the mixture induces the mixture to show a chiral smectic phase with a usefully high Ps.

It is desirable that the chiral tilted smectic phase of such a mixture has a helical pitch length that is comparable to the spacing of the electrodes of the electro-optical device in which it is to be used.

The pitch length of a chiral smectic mixture depends upon the "winding" effect of the optically active compounds included in it. A good measure of the winding effect of an optically active compound is the pitch length of the cholesteric (Ch) (chiral nematic (N*)) phase induced by the compound when it is mixed with a nematic liquid crystal material a small pitch indicating a powerful winding effect. By observation of the sense of the Ch pitch which is induced, the sense of the helical smectic pitch which would be induced by the compound may also be determined.

It is common practice to include two or more optically active compounds in a ferroelectric smectic liquid crystal mixture, one or more of which are dopants serving to induce a high Ps, and one or more of the others having a winding effect of an opposite sense to that of the dopant(s), but not necessarily inducing a high Ps. The other optically active compound(s) serve(s) to "unwind" the helical phase induced by the dopant(s) and hence can be used to control the $S_c^*$ pitch length. This effect is called "pitch compensation", and it is desirable that an optically active compound used in this way ("a pitch compensator") unwind the helical phase induced by the dopant has a powerful winding effect.

It is an object of the present invention to provide novel compounds which may be used as components of ferroelectric smectic liquid crystal mixtures, particularly as optically active dopants and pitch compensators. Other objects and advantages of the present invention will be apparent from the following description.

BRIEF DESCRIPTION OF THE FIGS.

Figure 1:
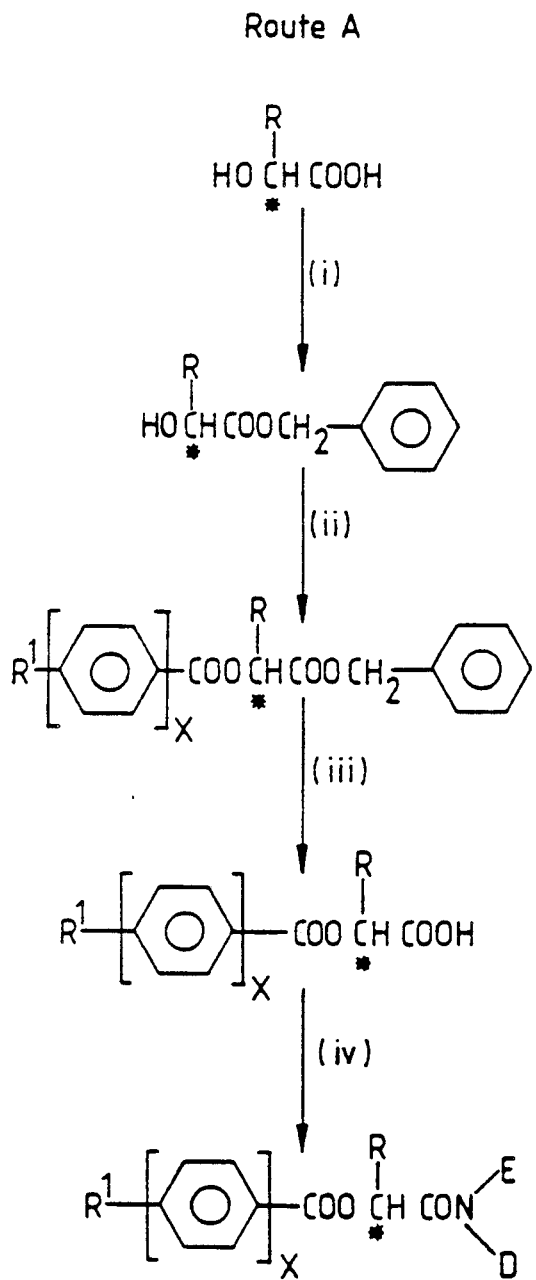
FIG. 1, 2 and 3 are synthetic routes for preparing the amides of this invention from optically pure enantiomers of the corresponding alpha-hydrocarboxylic acid or amino acid.

According to a first aspect of the present invention an optically active compound is provided, being an amide of formula I below:

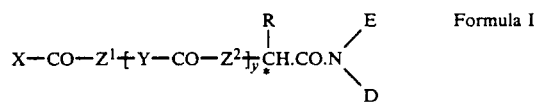

Formula I wherein X is a group having the structure:

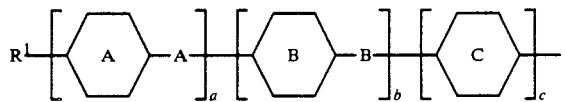

wherein Y is a group having the structure:

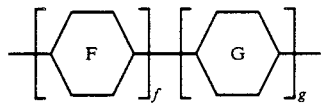

wherein $Z^1$ and $Z^2$ are independently selected from —O—, —NR°—, where R° is $C_{1-12}$ alkyl or hydrogen; wherein $R^1$ is hydrogen, alkyl, alkoxy, alkylcarbonyloxy, alkoxycarbonyl, hydrogen, halogen, CN, R°COOCH($CH_3$)COO or R°OOCH— ($CH_3$)OOC:

where A and B are independently selected from a single covalent bond, COO, OOC, $CH_2CH_2$, —N=N—, —N-(O)=N—:

wherein a, b, c, f, g and y are independently 0 or 1:

where R is methyl or phenyl:

and wherein D and E are independently selected from hydrogen, alkyl —$Y^1$-alkyl, —$Y^{11}$-alkoxy, wherein $Y^1$ and $Y^{11}$ are independentlyl selected from the structures from which Y may be selected, or D and E together with the N represent the residue of a heterocyclic N-containing ring system, wherein each of the cyclic groups

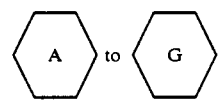

are independently selected from 1,4-linked phenyl optionally carrying one or more substituents and/or having one or two =CH— units replaced by nitrogen; 1,4-linked trans-cyclohexane optionally carrying one or more substituents and/or having one or two $CH_2$ groups replaced by oxygen, nitrogen or sulphur; or bicyclo(2,2,2) octane.

Many amides of Formula I are suitable for use as components of ferroelectric smectic liquid crystal mixtures as dopants but especially as pitch compensators. According to a further aspect of the invention there is therefore provided a ferroelectric smectic liquid crystal mixture which contains at least one amide of Formula I. Particular usefulness for use as a component of such a mixture is among the factors deciding the structural preferences discussed below.

Preferably y is O and Z' is —O—. Compound of this structure have the additional advantage of ease of synthesis.

Preferably R is methyl.

Preferably the amide of Formula I contains not more than three of the cyclic groups

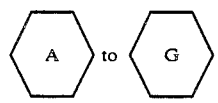

Preferably $R^1$ contains 1-12 carbon atoms and is alkyl or alkoxy, which may be n-alkyl or n-alkoxy, or branched (iso) or chiral alkyl or alkoxy. Preferred alkyl groups contain 5-12 carbon atoms, and preferred chiral alkyl groups are 2-methylbutyl and 2-methylheptyl.

Preferably $R^o$ when present contains 1-4 carbon atoms. Preferably all of the rings

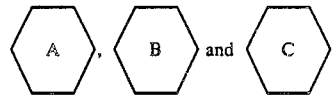

when present are phenyl and unsubstituted, out a preferred lateral substituent is fluorine.

Some preferred examples of structures for the acyl group of the amide of Formula I are listed in table 1 below, where the cyclic groups shown may carry substituents as defined above, particularly a lateral fluorine substituent. Structure 1a and 1p are especially preferred.

TABLE 1

TABLE 1-continued

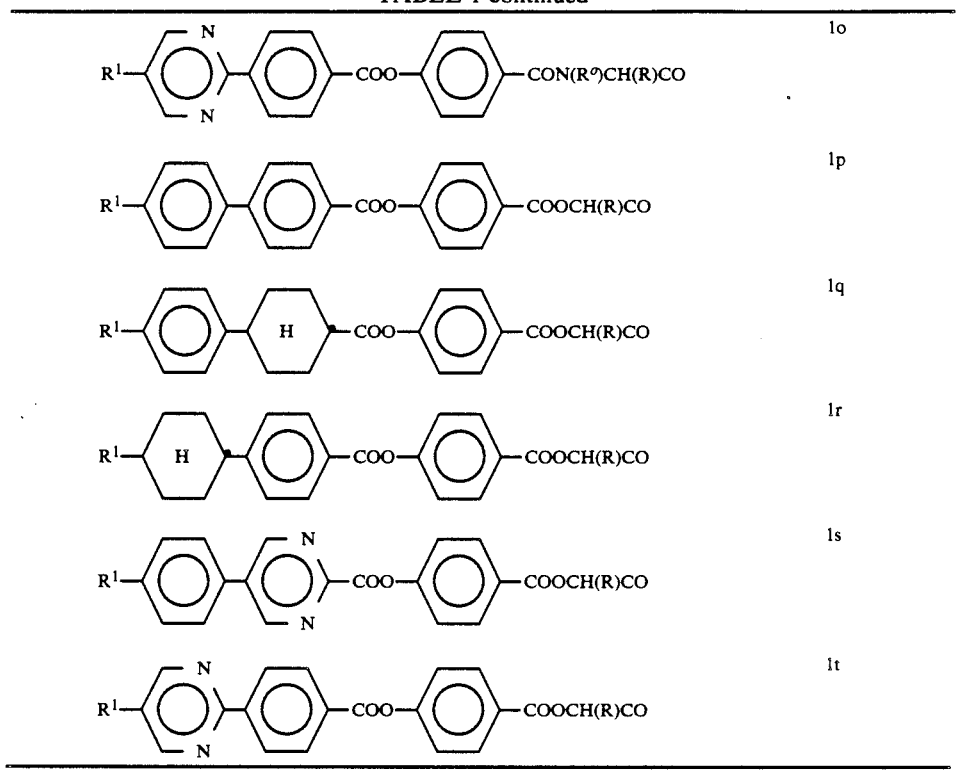

The group N(E)D may have a number of preferred structures encompassed by Formula I, as discussed below.

N(E)D may be a primary amine or anilino group, i.e.

—NHR' or

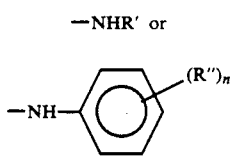

where R' is alkyl, especially n-alkyl containing up to 10 carbon atoms where n is 0 to 5 and where R" is alkyl or alkoxy especially n-alkyl or n-alkoxy containing up to 10 carbon atoms. R" when present preferably is in the para (4) position, and n is preferably 1 or 0.

N(E)D may be a secondary amine or anilino group, i.e.

—NR'R" or

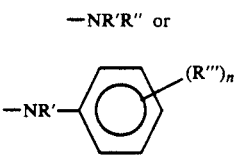

where R' and R" are independently alkyl containing up to 10 carbon atoms, and R'" is alkyl or alkoxy containing up to 10 carbon atoms. R', R" and R'" are preferably n-alkyl or n-alkoxy containing up to 6 carbon atoms. n is 0-5, preferably 0 or 1 and R'" when present is preferably in the para (40 position.

When N(E)D represents a heterocyclic N- containing ring system it is preferably a five or six membered heterocyclic ring system, which may contain a second nitrogen or an oxygen atom in the ring. Some preferred heterocyclic ring systems from which N(E)D may be selected include the following:

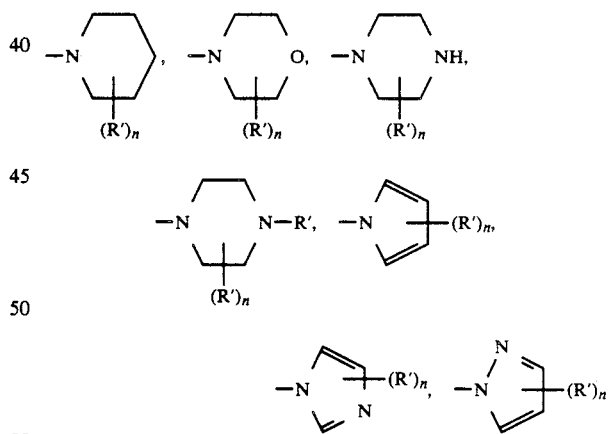

where $(R')_n$ indicates that one or more substituents R' may be present on the ring, R' being selected from alkyl, alkoxy, halogen, $CF_3$ and CN. When present R' is preferably n-alkyl containing up to 8 carbon atoms, especially methyl. n may have valves from 0 up to the total number of available substitution positions on the ring, but is preferably 0, 1 or 2.

Amides of formula I may be prepared from the appropriate base H—N(E)D and the appropriate carboxylic acid by well known methods for the synthesis of amides.

As the asymmetric centre indicated by * in formula I is either in an alpha-hydroycarboxylic acid group (e.g. a lactate group —O—CH($\overset{*}{\text{C}}$H₃)CO—) or in an amino acid group (e.g. —NH.CH(CH₃)CO—) it is convenient to start the preparation of the amides from the optically pure enantiomes of the alpha-hydroxycarboxylic acid or amino acid.

Figure 2:
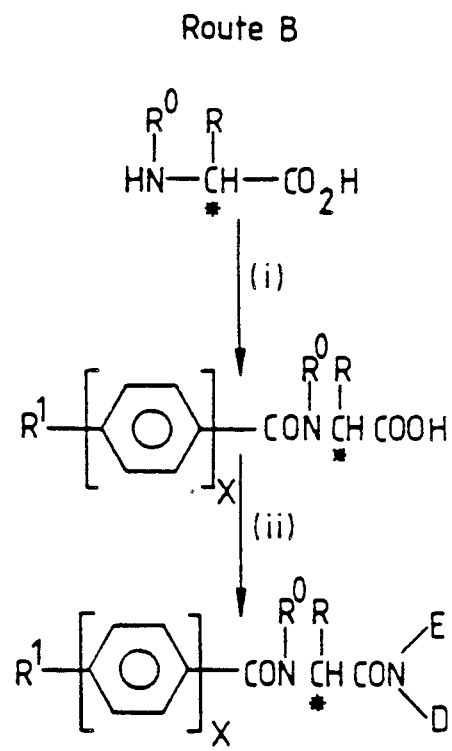
Figure 3:
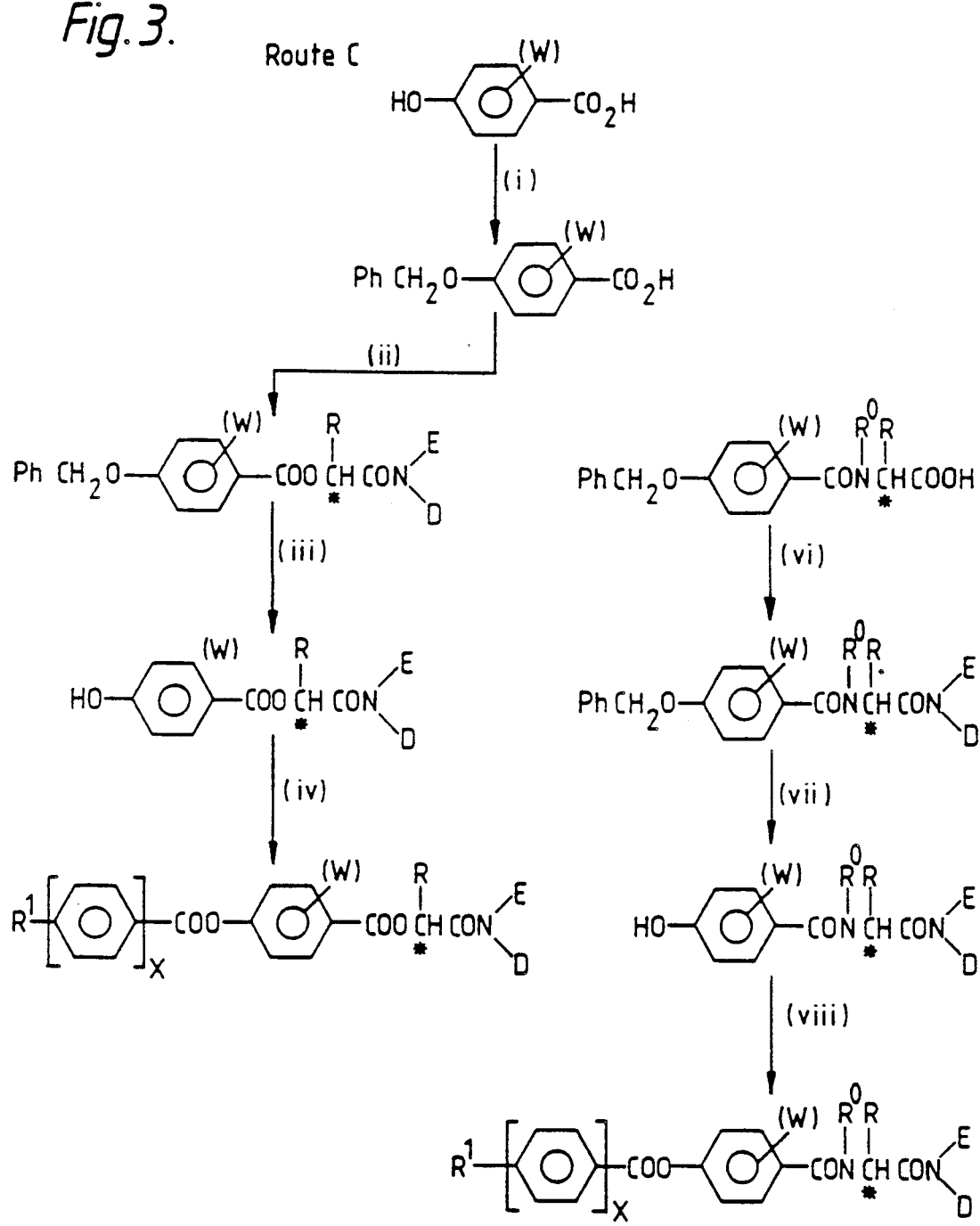

Some suitable generally applicable routes are routes A, B and C shown in FIGS. 1, 2 and 3, where x is 1, 2 or 3 and R' is alkyl or alkoxy.

Figure 4:
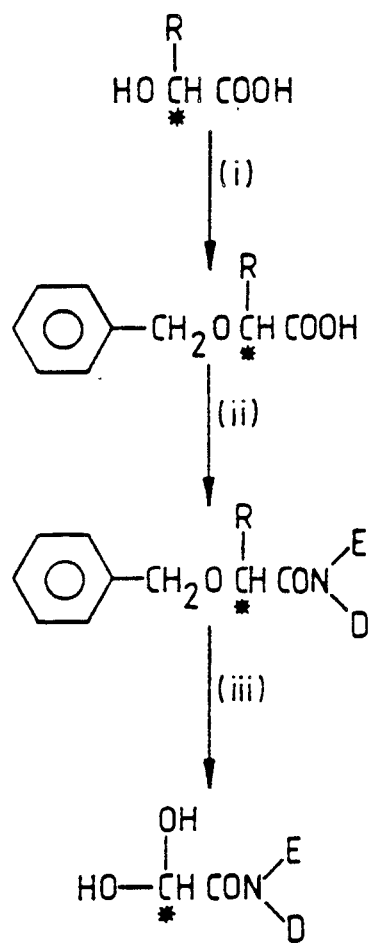
FIG. 4 shows the synthetic route for preparing the specific amide used in step C(ii) of FIG. 3.

The amide HOCH(R)CON$_D^E$ used in step C(ii) may be prepared for example form the corresponding alpha-hydroxycarboxylic acid by a reaction analogous to step A(iv), with the preliminary precautionary step of protecting the alpha-hydroxyl group as shown for example in route D in FIG. 4.

In routes A, B, C and D the general procedure is as below:

Route A
(i) 90% aq methanol, 20% aq Cs₂CO₃, pH 7; PhCH₂Br, DMF
(ii) a. when x is 2,

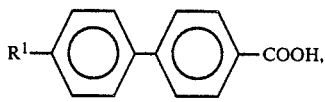

N,N-dicyclohexylcarbodiimide (DCC), 4-(N-pyrrolidino)pyridine (N—PPy), CH₂Cl₂ b. when x is 3,

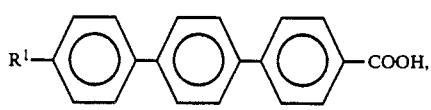

SOCl₂, Et₃N, CH₂Cl₂
(iii) 5% Pd-C, ethyl acetate, H₂
(iv) (CH₃)₃C.COCl,

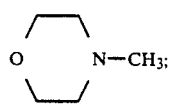

H—N$_D^E$, C₆H₅CH₃.
Route B
(i)

oxalyl chloride, DMF; amino acid, CH₂Cl₂, NaHCO₃
(ii) as in route A step (iv)
Route C
(i) aq NaOH, ethanol, PhCH₂Br
(ii) as route A step (iv), HOCH(R)CON$_D^E$
(iii) 5% Pd-C, ethanol, H₂
(iv) as route A step (ii)
(v) as rout B step (i), HN(R°)CH(R)COOH
(vi) as route A step (iv)
(vii) as route C step (iii)
(viii) as route A step (ii)
Route D
(i) aq NaOH, ethanol, PhCH₂Br
(ii) as step A(iv)

(iii) 5% Pd-C, ethanol, H₂
Many of the starting materials for Routes A, B and C are commercially available in optically pure enantiomeric forms.

. For example the alpha hydroxycarboxylic acids lactic acid and mandelic acid, which may be used in steps A(i), and (ii):

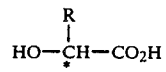

R=CH₃=lactic acid
R=C₆H₅=mandelic acid are available from the Aldrich Chemical Company.

The amino acid used in Routes B and C may also be a commercially available naturally occurring amino acid, such as those listed in Table 2 below, in which the group R which is present in the structure is indicated.

TABLE 2

| amino acid | R |
|---|---|
| Glycine | H |
| α-Alanine | CH₃ |
| Valine | (CH₃)₂CH |
| Leucine | (CH₃)₂.CH.CH₂ |
| Isoleucine | CH₃.CH₂.CH(CH₃) |

The amino acids listed in Table 2 all have hydrogen as R°. To prepare amino acids where R° is alkyl, the alkylation methods described by E. Fischer and W. Lipschitz, "Chem. Ber" (1915) p. 360-378 where the preparation of N-methylalanine, N-methylleucine, N-methylphenylalanine and N-methyl-tyrosine are described. Examples and further discussion of methods similar to step B(i) and C(v) are given in Applicant's copending GB 86200111 and PCT/GB86/00599.

Examples of suitable bases for use in Routes A and C and C(vi), i.e. compounds H—N(E)D are listed below in Table 3.

TABLE 3

H—NHC$_n$H$_{2n+1}$ for all values of n=1 to 12 inclusive.

H—N(C$_n$H$_{2n+1}$)(CmH$_{2m+1}$) for all values of n and m independently selected from 1 to 12 inclusive.

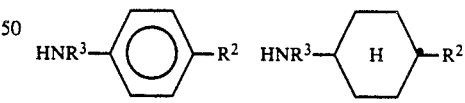

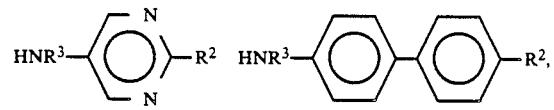

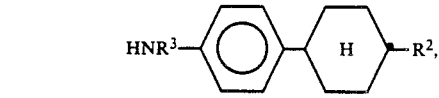

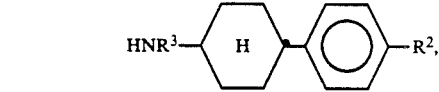

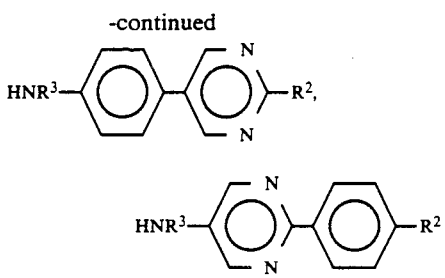

where $R^3$ is hydrogen or $C_1$-$C_{12}$ alkyl, e.g. n-alkyl or chiral alkyl and $R^2$ is independently selected from the groups from which $R^1$ is selected. $R^3$ is preferably methyl.

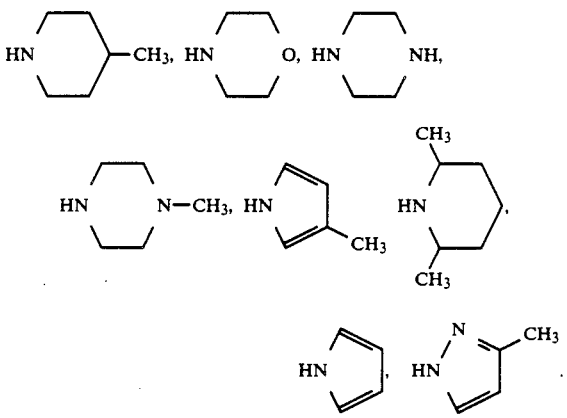

A ferroelectric smectic liquid crystal mixture of the invention will normally contain at least one smectic host (or defined above). Some preferred classes of compounds from which the smectic host compound(s) may be selected are shown in table 4 below many of which are commercially available. Hosts containing one or more compounds of formulas 4.1 or 4.2 are particularly preferred.

The mixture will contain at least one amide of Formula I, which may be present as a racemic mixture of tis optical enantiomers but is preferably present as an optically active enantiomer for example to function as a chiral dopant.

In a preferred embodiment the mixture also contains at least one other optically active smectogenic compound, for example to function as a chiral dopant (as defined above). By "smectogenic" is meant that the compound wither shows a smectic phase, especially smectic C, or else that it may be mixed with a smectic material to result in a smectic mixture.

If the mixture contains such a optically active compound as well as an amide of Formula I, then preferably the sense of the helical pitch induced in the smectic phase by at least one of the smectogenic optically active compounds is opposite to that induced by at least one of the amides of Formula I, so that the amide of Formula I functions as a pitch compensator to control, e.g. to lengthen or shorten the helical pitch of the S* phase induced by the smectogenic compound.

Preferably when used as a pitch compensator only one optically active amide of formula is included in the mixture, together with only one chiral dopant, the dopant not being an amide of Formula I.

A large number of chiral dopants is known; some preferred classes of chiral dopants which may be used together with an amide of Formula I as pitch compensator are listed in table 5, those of structure 5.5 being especially preferred particularly those with N=0 and $R^E$ being branched alkyl.

Other known chiral dopants include the optically active compounds discosed in EPA's 86306261, 0110299, 0152217, 0164814, 0174191, 136845, 168963, 160416, 167328, 115693, 153826, 131373, 175591, 157519, 159872; GB 8629322; PCT GB/87/00131 and WO 86/0087 among others.

TABLE 4

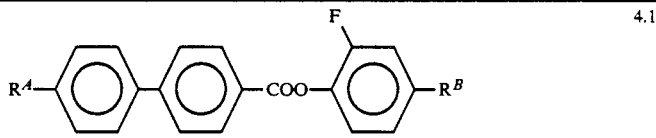

4.1

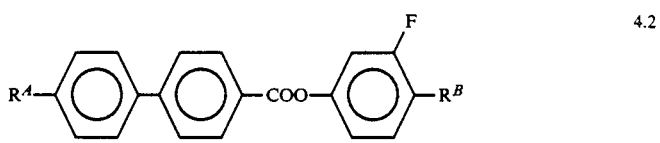

4.2 racemic

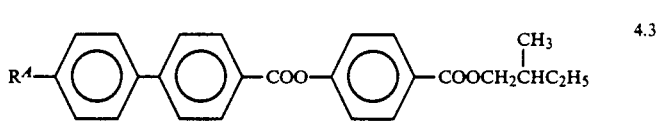

4.3 racemic

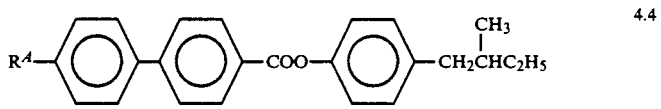

4.4

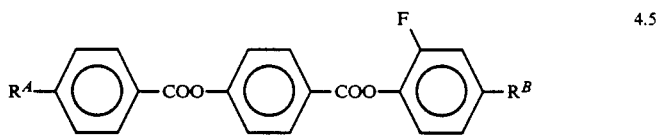

4.5

TABLE 4-continued

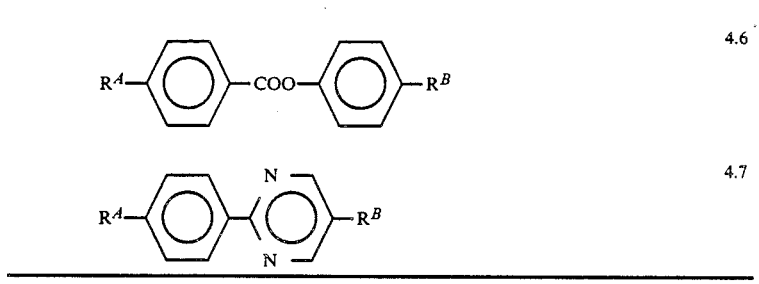

where $R^A$ and $R^B$ are $C_{1-12}$ n-alkyl or n-alkoxy.

TABLE 5

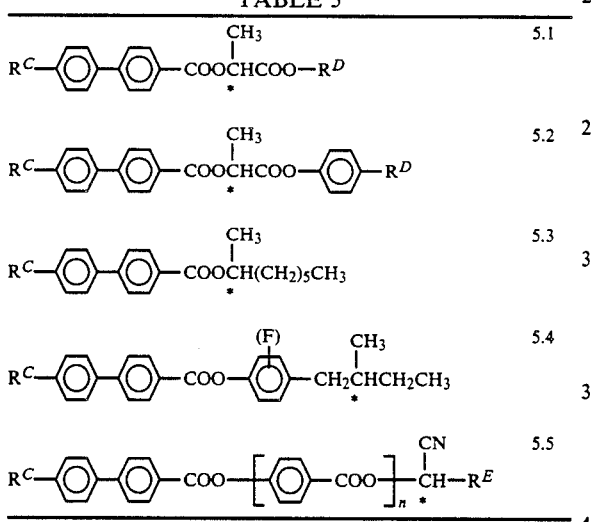

where $R^C$ may by n-alkyl or n-alkoxy, and $R^D$ may be n-alkyl or n-alkoxy, $R^C$ and $R^D$ independently containing 1-12 carbon atoms, and $R^E$ is $C_{1-12}$ n-alkyl, branched chain alkyl, cycloalkyl or phenylalkyl. n in structure 5.5 is 0 or 1.

A further advantage of the amides of Formula I is that when included in a ferroelectric smectic liquid crystal mixture, especially as pitch compensators, in many cases they are particularly helpful in suppressing undesirable smectic phases which might otherwise occur at low temperatures. It is sometimes desirable that the mixture does show an $S_A$ phase at a temperature above the $S_c^*$ phase, for example to assist in alignment of the liquid crystal material, and in such cases it may be desirable to include an additive such as a compound of general formula

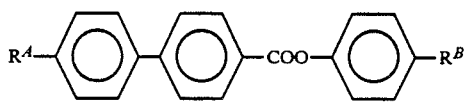

where $R^A$ and $R^B$ are as defined above to promote the appearance of such an $S_A$ phase. In other cases it may be desirable to include other additives to further suppress the appearance of low temperature $S_A$ or $S_B$ phases, such as compounds of general structure:

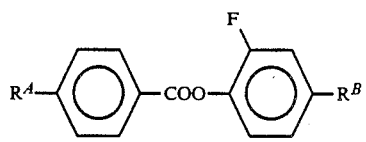

where $R^A$ and $R^B$ are as defined above.

Typically when an amide of Formula I is used as a chiral dopant in a ferroelectric smectic liquid crystal mixture, the mixture has the following composition:

| | |
|---|---|
| One or more host compounds, eg table 4 compounds. | 1 to 99 weight % (preferably up to 90%) |
| One or more optically active amides of Formula I | 1 to 30 weight % |
| Additives, eg to control other smectic phases | 0 to 20 weight % |

Typically when an amide of Formula I is used as a pitch compensator together with a chiral dopant not being an amide of Formula I, the mixture has the following composition:

| | |
|---|---|
| One or more host compounds, eg table 4 compounds | 1 to 99 weight % (preferably up to 90%) |
| One or more chiral dopants, eg table 5 compounds | 1 to 30 weight % |
| Optically active amide of Formula I | 0.001 to 10 weight % (preferably 0.01 to 2.5 weight %) |
| Additives, eg to control other smectic phases | 0 to 20 weight % |

The total in each case being 100 weight %.

The relative amounts of each of the above components in the mixture will depend upon the use for which the mixture is intended and the composition can be tailored to fit the requirements. Generally the Ps of the mixture is directly proportional to the amount of the chiral dopant in the mixture, and the unwinding effect of a pitch compensator is proportional to the amount of the compensator present.

Such a mixture may be used in any of the known types of ferroelectric smectic liquid crystal electro-optic device, for example as described in Appl. Phys. Lett. 36, (1980) p. 899.

An example of such a device is the "Clark Lagerwall Device", described in Reference 1, and also in "Recent Developments in Condensed Matter Physics" 4, p. 309, (1981) (Reference 3). The physics of this device, and methods of constructing one, are well known. In practice such a device usually consists of two substrates, at least one of which is optically transparent, electrodes on the inner surfaces of the substrates and a layer of the liquid crystal material sandwiched between the substrates.

The Clark Lagerwall device uses a layer of liquid crystal material between the substrates of a thickness comparable to or less than the helical pitch of the S* configuration, which causes the helix to be unwound by surface interactions. In its unwound state the material has two surface stabilized states with director orientations (is molecular tilt direction) at twice the tilt angle to one another, and also permanent dipole orientations perpendicular to the substrates but in opposite directions.

An alternative approach to providing cells for a Clark-Lagerwall device having a thicker layer of liquid crystal material is to use an applied electric field to induce homogeneous alignment through interaction with the dielectric anistropy of the liquid crystal material. This effect requires a chiral smectic material having a negative dielectric anisotropy e.g. provided by incorporation of a compound having a lateral halogen or cyano substituent. Such a compound may itself be chiral or non-chiral and smectic or non-smectic.

In general chiral smectic C materials ($S_c^*$) are used in these displays because these are the most fluid, but in principle the more ordered chiral smectics could also be used. A pleochroic dye may also be incorporated in the liquid crystal material to enhance the electro-optic effect.

Such a device incorporating compounds of Formula I offers the possibility of a high switching speed of a few microseconds—as demonstrated in Reference 3—together with bistable storage capability; consequently it is likely to have important application in displays, optical processing devices, and optical storage devices.

According to the present invention in a further aspect, there is provided an electro-optical device, operating by a ferroelectric effect in a liquid crystal material, wherein the liquid crystal material is a mixture of compounds at least one of which is a compound of Formula I.

The device may, for example, be a Clark-Lagerwall device as described above, and may comprise two substrates at least one of which is optically transparent, electrodes on the inner surfaces of the substrates, and a layer of the liquid crystal material sandwiched between the substrates.

The liquid crystal mixtures incorporating a compound of Formula I are especially suited for use in rapidly switched large screen (e.g. A4 size) displays, such as are used in portable computers, desk top calculators and visual display units, and by using appropriately shaped substrates and electrodes the electro-optical device of the invention may be made in this form.

In this description and the accompanying examples the following symbols and abbreviations are used:

 and Ph represent a phenyl (benzene) ring.

 represents trans cyclohexyl.

| | |
|---|---|
| $[\alpha]_D^{24}$ | optical rotation angle at 24° C. using sodium D line. |
| tlc | thin layer chromatography. |
| c | concentration. |
| S, R | designations of absolute configuration of chiral centre. |
| (+), (−) | designations of sense of optical rotation of an optically active (chiral) material. |
| | All temperatures are given in °C. |

The invention will now be described by way of example only with reference to FIGS. 1 to 4 which illustrate preparative routes for compounds of formula 1 and FIG. 5 which shows a sectional view of a liquid crystal electro-optic display device.

EXAMPLE 1 Route A

Step 1A(i) Preparation of

   (A)

S-(+)- Lactic acid (18.0 g) was dissolved in methanol (360 cm³) and water (40 cm³) was added. The solution was titrated to pH 7.0 (pH meter or pH paper) with a 20% aqueous solution of caesium carbonate (ca. 160 cm³). The solvent was removed under reduced pressure at 50° C. and the residue was re-evaporated twice from N,N-dimethylformamide (DMF) (2×100 cm³) at the same temperature. The white solid caesium salt obtained was stirred with benzyl bromide (34.2 g) in DMF (300 cm³) for 15 h. The caesium bromide was filtered off, the filtrate was concentrated and then ether was added to the residue (150 cm³). The organic layer was washed successively with water (100 cm³), saturated NaHCO₃ (500 cm³) and water (100 cm³) and finally dried (MgSO4). After removal of the solvent, the residual liquid was distilled under reduced pressure to afford the product as colorless liquid, yield 28.8 g (80%), bp 96° C. (0.05 mm Hg), $[\alpha]_D^{24}$ −12.9 (c 0.01, CHCl₃).

Note: Commercially available S-(+)- lactic acid (Aldrich) was redistilled before it was used.

Ref. S. S. Wang, J. Org. Chem. 41, 3258, (1976).

Step 1A(ii) Preparation of

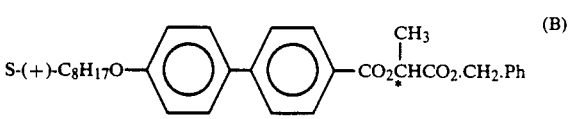   (B)

To a stirred mixture of 4-octyloxybiphenyl —4'-carboxylic acid (10.8 g), S-(−)-benzyl lactate (A) (5.9 g) and 4-pyrrolidinopyridine (N-PFY) (0.49 g) in sieve-dried CH₂Cl₂ (250 cm³), a solution of N,N-dicyclohexylcarbodiimide (DCC) (7.5 g) in sieve dried CH₂Cl₂ (50 cm³) was added slowly. The reaction mixture was stirred for 5 h at room temperature. The N,N-dicyclohexylurea (DCU) was filtered off and the filtrate was washed successively with water (100 cm³), 5% aqueous acetic acid (100 cm³), water (2×100 cm³) and finally dried (MgSO4). After removal of the solvent, the crude diester was purified by column chromatography using silica gel and dichloromethane:petroleum fraction (bp 60°–80° C.) (4:1) as eluent. The product was crystallised from ethanol. Yield 11.1 g (69%), mp 62.5° C. $[\alpha]_D^{24}+24.7$ (c 0.01, CHCl$_3$).

Ref. A. Hassner & V. Alexanian, Tetrahedron Letters 46, 4475, (1978).

Step 1A(iii) Preparation of

 (C)

Compound (B) (11.0 g) was dissolved in ethyl ethanoate (150 ml). 5% Pd on charcoal (200 mg) was added and the mixture was stirred under an atmosphere of hydrogen overnight. After hydrogenation (500 cm$^3$ of hydrogen consumed) was completed, the catalyst was filtered off and the filtrate was evaporated to dryness. The colourless solid residue (single sport by tlc) was crystallised from petroleum fraction (bp 60°–80° C.) to give the required carboxylic acid (C) as colourless needles. Yield 8.6 g (95%), mp 126° C., $[\alpha]_D^{24}+40.8°$ (c 0.01 CHCl$_3$).

Step 1A(iv) Preparation of

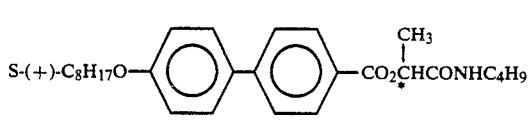 (D)

A stirred solution of compound (C) (1.59 g 0.004 mol) and N-methylmorpholine (0.40 g, 0.004 mol) in sodium dried toluene (30 ml) was cooled to 0° C. and trimethylacetyl chloride (0.48 g, 0.004 mol) in sodium-dried toluene (5 ml) was added dropwise. After 2 hr at 0° C., n-butylamine (0.35 g, 0.0048 mol) in sodium-dried toluene (5 ml) was added dropwise to the reaction mixture. The mixture was then stored at 8° C. overnight.

The mixture was then diluted with toluene (40 ml) and washed successively with 5% aqueous NaHCO$_3$, water, 5% aqueous HCl and water and finally dried (MgSO$_4$).

After removal of the solvent, the crude amide was purified by column chromatography on silica gel, using chloroform:ethyl ethanoate (95:5) as eluent. The product was recrystallised from ethanol:ethyl ethanoate (3:1) to afford compound D as colourless needles Yield 1.15 g (64%) mp 168° C. $[\alpha]_D^{24} = +62.4°$ (in CHCl$_3$, conc 0.01).

Analogous amides were prepared using the appropriate amine instead of n-butylamine in step 1A(iv), and the appropriate carboxylic acid. Properties of some of these are listed in tables 6 and 7 below.

TABLE 6

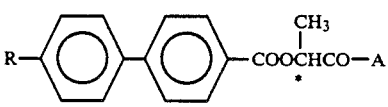

| R | A | Mp | $[\alpha]_D^{24}$ | N*(L) | N*(W) |
|---|---|---|---|---|---|
| 8.0 | NHBu | 168 | +62.4 | | |
| 9 | NMeBu | 69 | +51.3 | 0.121 | 0.120 |
| 10 | NMeEt | 71.5 | +48.3 | 0.062 | 0.081 |

TABLE 6-continued

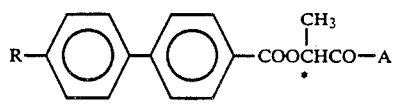

| R | A | Mp | $[\alpha]_D^{24}$ | N*(L) | N*(W) |
|---|---|---|---|---|---|
| 8.0 | ![cyclohexyl-N] | 100.0 | +56.8 | 0.061 | 0.075 |
| 10 | ![cyclohexyl-N-Me] | 82.0 | +56.0 | 0.028 | 0.033 |
| 8.0 | ![cyclohexyl-N-Pent] | 96.5 | +60.0 | | |
| 8.0 | ![cyclohexyl-N-O] | 109.0 | +53.3 | | |
| 9 | ![cyclohexyl-N-O] | 93.0 | +54.1 | 0.066 | 0.075 |
| 10 | ![cyclohexyl-N-N-Me] | 89.0 | +59.1 | | |
| 10 | ![cyclohexyl-N-Me,Me] | 65.5 | +68.0 | 0.096 | 0.107 |
| 10 | ![pyrazole-Me] | 48.0 | +75 | 0.060 | 0.058 |
| 10 | ![NH-phenyl-Bu] | 151.0 | +87.7 | 0.066 | 0.079 |
| 10 | ![NH-phenyl-OMe] | 74.0 | +179.08 | | |
| 10 | ![N,N-Me,Me pyrazole] | | | 0.039 | 0.040 |
| 10 | ![NH-phenyl-Me] | | | 0.028 | 0.033 |

TABLE 7

R—⟨phenyl⟩—⟨phenyl⟩—COO—⟨phenyl⟩—COOCHCO—A
                                        |
                                        CH$_3$

| R | A | Liq Cryst Transitions | $[\alpha]_D^{24}$ | N*(L) | N*(W) |
|---|---|---|---|---|---|
| 9.0$^a$ | NMeBu | C 114 I (111) S$_c$* | +29.6 | | |
| 9.0$^b$ | ⟨N-methylpiperidinyl-Me⟩ | C 140 I | +35.0 | 0.091 | 0.10 |
| 9.0 | ⟨pyridazinyl-Me⟩ | C 79 158 BP 159 I | +40.5 | 0.077 | 0.069 |

Note:
$^a$the S$_c$* phase was monotropic.
$^b$appears to form a Ch phase at ca 80° C. (on rapid cooling) but recrystalisation occurred almost instantaneously at the same temperature.

In tables 6 and 7 the following abbreviations are used:
R=8.0 means C$_8$H$_{17}$O, 9 means C$_9$H$_{19}$, 10 means C$_{10}$H$_{21}$etc.
Me=methyl
Et=ethyl
Bu=n-butyl
Pent=n-pentyl
Mp=melting point (°C.)
$[\alpha]_D^{24}$=optical rotation at 24° C., Na-D line, in Chloroform.
N*=Chiral nematic pitch ($\mu$) in E7 at room temperature measured by (L)=laser diffraction, (W)=carnot wedge
C=solid crystal
I=isotropic liquid
BP=blue phase
Ch=cholesteric (chiral nematic)

E7 is a nematic liquid crystal mixture having a composition:

n-C$_5$H$_{11}$—⟨phenyl⟩—⟨phenyl⟩—CN  51 wt % n-C$_7$H$_{15}$—⟨phenyl⟩—⟨phenyl⟩—CN  25 wt % n-C$_8$H$_{17}$O—⟨phenyl⟩—⟨phenyl⟩—CN  16 wt % n-C$_5$H$_{11}$—⟨phenyl⟩—⟨phenyl⟩—⟨phenyl⟩—CN  8 wt %

The Ps and tilt angle of some of the above compounds was measured in a mixture with a smectic material having a composition:

C$_8$H$_{17}$O—⟨phenyl⟩—⟨phenyl⟩—COO—⟨phenyl-F⟩—C$_5$H$_{11}$  30 wt %

C$_8$H$_{17}$—⟨phenyl⟩—⟨phenyl⟩—COO—⟨phenyl-F⟩—C$_5$H$_{11}$  30 wt %

C$_7$H$_{15}$O—⟨phenyl⟩—⟨phenyl⟩—COO—⟨phenyl-F⟩—C$_5$H$_{11}$  30 wt %

This mixture is referred to hereafter as 'H1'

-continued

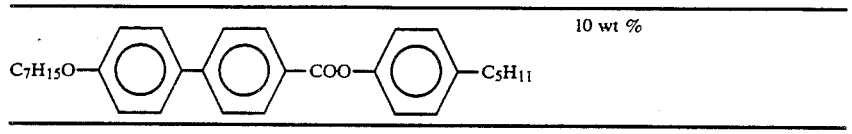 10 wt %

The Ps was measured at a temperature 10° C. below the $S_c^*$-$S_A$ transition of the mixture, and extrapolated to 100% of the compound (ext Ps).

| Compound | ext Ps | Tilt Angle (°) |
|---|---|---|
| 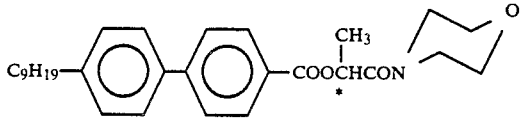 | 35 | 18 |
| 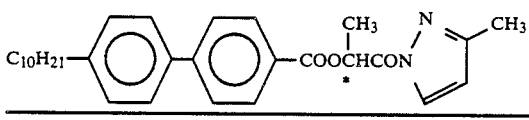 | 7.5 | 8 |

Tables 6 and 7 therefore show the extremely small Ch pitch of the compounds, and their suitability for inclusion in a ferroelectric smectic liquid crystal material is shown by selected examples giving a Ps in a smectic mixture.

The compounds wherein the group N(E)D was

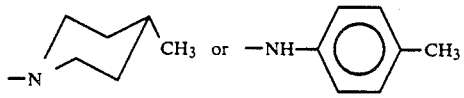

showed exceptionally small Ch pitches.

EXAMPLE 2

A ferroelectric smectic liquid crystal mixture was prepared having the following composition:

| H1 (as defined above) | 80 wt % |
|---|---|
| 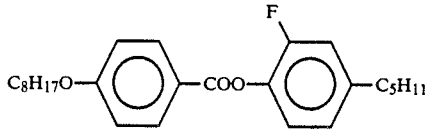 | 10 wt % |
| 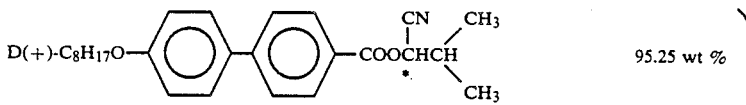 95.25 wt % <br>  4.75 wt % | 10 wt % |

The optical activity of the two optically active compounds was chosen so that the amide functioned as a pitch compensator to the dopant cyano-compound.

This mixture had liquid crystal transition temperatures (°C):

I 124 Ch 94.9 $S_A$59.6 $S_c^*$ and was $S_c^*$ at room temperature and lower. The mixture therefore contained less than 0.5 weight % of the amide pitch compensator.

An example of the use of a compound of Formula I in a liquid crystal material and device embodying the present invention will now be described with reference to FIG. 5.

Figure 5:
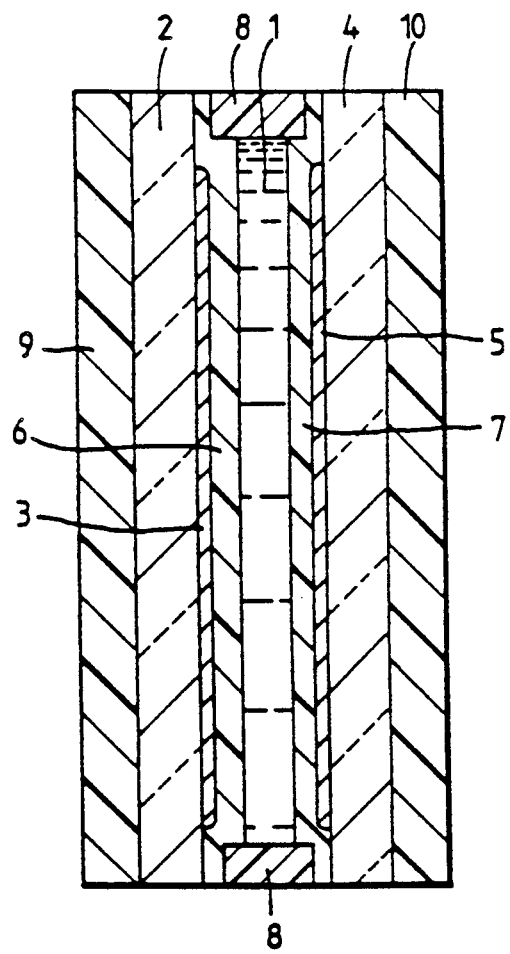
FIG. 5 is a sectional view of a liquid crystal electro-optic display device.

In FIG. 5 a liquid crystal cell comprises a layer 1 of liquid crystal material exhibiting a chiral smectic phase sandwiched between a glass slide 2 having a transparent conducting layer 3 on its surface, e.g. of tin oxide or indium oxide, and a glass slide 4 having a transparent conducting layer 5 on its surface. The slides 2,4 bearing the layers 3,5 are respectively coated by films 6,7 of a polyimide polymer. Prior to construction of the cell the films 6 and 7 are rubbed with a soft tissue in a give direction the rubbing directions being arranged parallel upon construction of the cell. A spacer 8 e.g. of polymethyl methacrylate, separates the slides, 2,4 to the required distance, e.g. 5 microns. The liquid crystal material is introduced between the slides 2,4 to the required distance, e.g. 5 microns. The liquid crystal material 1 is introduced between the slides 2,4 by filling the space between the slides 2, 4 and spacer 8 and sealing the spacer 8 in a vacuum in a known way. Preferably the liquid crystal material is in the smectic A, nematic or isotropic liquid phase (obtained by heating the material) when it is introduced between the slides 2,4 to facilitate alignment of the liquid crystal molecules with the rubbing directions on the slides 2,4.

A polarizer 9 is arranged with its polarization axis parallel to the rubbing direction on the films 6,7 and an analyzer (crossed polarizer) 10 is arranged with its polarization axis perpendicular to that rubbing direction.

When a square wave voltage (from a conventional source not shown) varying between about +10 volts and −10 volts is applied across the cell by making contact with the layers 3 and 5 the cell is rapidly switched upon the change in sign of the voltage between a dark state and a light state as explained above.

In an alternative device (not shown) based on the cell construction shown in FIG. 5 the layers 3 and 5 may be selectively shaped in a known way, e.g. by photoetching or deposition through a mask, e.g. to provide one or more display symbols, e.g. letters, numerals, words or graphics and the like as conventionally seen on displays. The electrode portions formed thereby may be addressed in a variety of ways which include multiplexed operation.

The chiral smectic liquid crystal mixture of example 2 above is suitable for use as the layer 1 of liquid crystal material in this device.

We claim:

1. An amide having a formula:

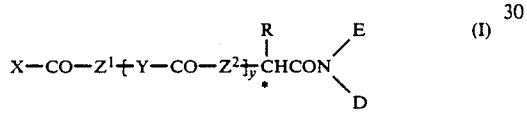

where X has the structure:

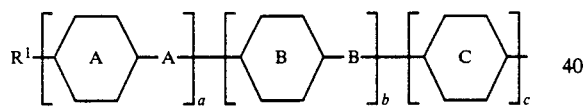

Y has the structure:

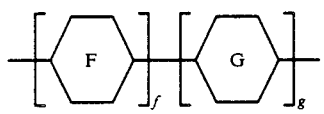

where
$Z^1$ and $Z^2$ are independently selected from —O— and —NR°—;
R° is $C_{1-12}$ alkyl or hydrogen;
$R^1$ is hydrogen, alkyl, alkoxy, alkylcarbonyloxy, alkoxycarbonyl, hydrogen halogen, CN, R°COOCH($CH_3$)COO or R°OOCH($CH_3$)OOC;
A and B are independently selected from a single covalent bond, COO, OOC, $CH_2CH_2$, —N=N—, —N(O)=N—;
a, b, c, f, g and y are independently 0 or 1;
R is methyl or phenyl;
D and E are independently selected from hydrogen, alkyl, —Y′-alkyl, and —Y″-alkoxy, where Y′ and Y″ are independently selected from the structures from which Y may be selected, or D and E together with the N represent the residue of a heterocyclic N-containing ring system; and each of the cyclic groups A, B, C, D, F, G are individually and independently selected from
1,4-linked phenyl,
1,4-linked phenyl carrying one or more fluorine atoms or having one or more =CH— units replaced by nitrogen,
1,4-linked trans-cyclohexane,
1,4-linked transcyclohexand carrying one or more fluorine atoms, or having one or more $CH_2$ groups replaced by oxygen, nitrogen or sulfur, or
bicyclo (2,2,2) octane.

2. An amide according to claim 1, y is O and $Z^1$ is —O—.

3. An amide according to claim 2, wherein R is methyl.

4. An amide according to claim 3, wherein $XCOZ^1$ has a structure selected from

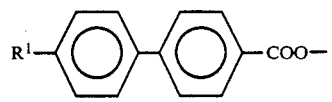

and

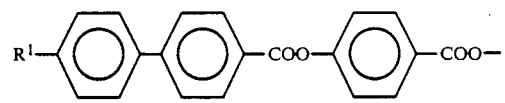

5. An amide according to claim 4 wherein $R^1$ is n-alkyl or n-alkoxy containing 1 to 12 carbon atoms.

6. An amide according to claim 2 wherein —N(E)D is a primary amine or primary anilino group having a structure selected from

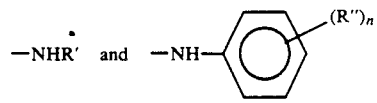

where R′ is alkyl and R″ is alkyl or alkoxy, n is 0 to 5, and R′ and R″ contain up to 10 carbon atoms.

7. An amide according to claim 6, wherein R′ is $C_{1-6}$ n-alkyl and R″ is $C_{1-6}$ n-alkyl or n-alkoxy, n is 1 and R″ is in the para (4) position.

8. An amide according to claim 2, wherein —N(E)D is a secondary amine or anilino group having a structure selected from

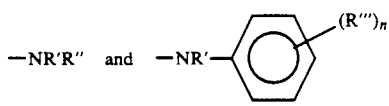

where R′ and R″ are independently alkyl containing up to 10 carbon atoms, and R‴ is alkyl or alkoxy containing up to 10 carbon atoms and n is 0 to 5.

9. An amide according to claim 8, wherein R′ and R″ are selected from $C_{1-6}$ n-alkyl and R‴ is selected from $C_{1-6}$ n-alkyl and n-alkoxy, n is 1 and R‴ is in the para (4) position.

10. An amide according to claim 2 wherein —N(E)D represents a 5 or 6 membered heterocyclic ring system which may contain a second nitrogen or an oxygen atom in the ring system.

11. An amide according to claim 10 wherein the heterocyclic ring system has a structure selected from the following:

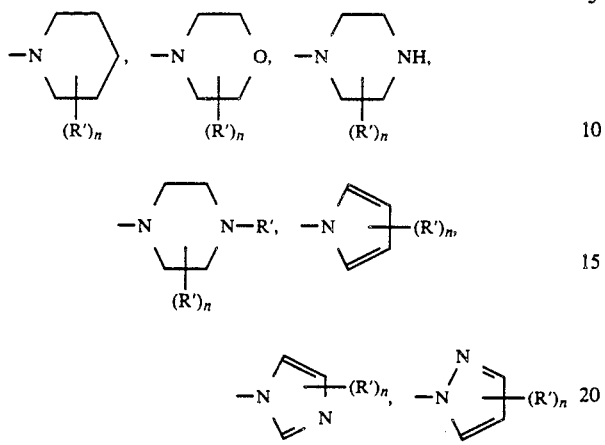

where R' is a substituent selected from alkyl, alkoxy, halogen, CF$_3$ and CN$_9$ and n may have valves from 0 up to the total number of available substitution positions on the ring.

12. An amide according to claim 11, wherein n is 0, 1 or 2 and R' is n-alkyl containing up to 8 carbon atoms.

13. A ferroelectric smetic liquid crystal material being a mixture of at least two compounds, wherein at least one of the compounds is an amide as claimed in any one of claims 1 to 3.

14. A ferroelectric smetic liquid crystal material being a mixture of at least two compounds, wherein at least one of the compounds is an optically active amide as claimed in any one of claims 4 to 12.

15. A material according to claim 14, wherein the amide has a structure in which N(E)D is selected from:

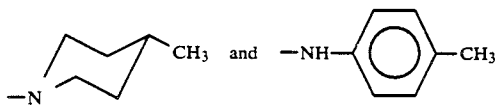

16. A material according to claim 14 wherein it contains at least one compound of general formula

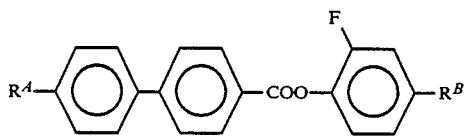

where $R^A$ and $R^B$ are independently C$_{1-12}$ n-alky or n-alkoxy.

17. A material according to claim 14 wherein the material contains at least one optically active smectogenic compound which is not an amide of Formula I.

18. A material according to claim 17 wherein the smectogenic compound is selected from compounds having a general formula

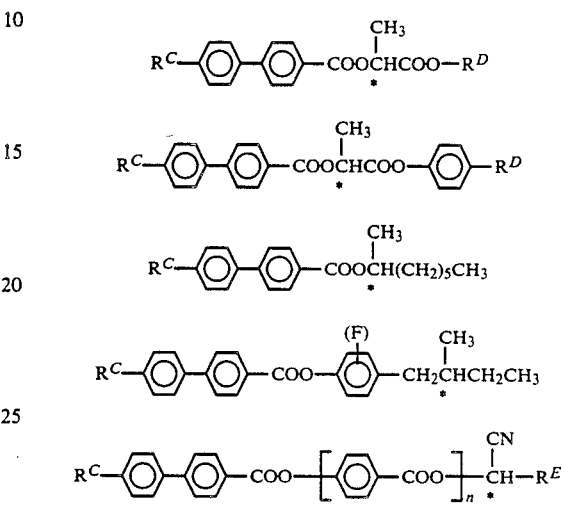

where $R^C$ may be n-alkyl or n-alkoxy, and $R^D$ may be n-alkyl or n-alkoxy, $R^C$ and $R^D$ independently containing 1-12 carbon atoms, and $R^E$ is C$_{1-12}$ n-alkyl, branched chain alkyl, cycloalkyl or phenylalkyl and n is 0 or 1.

19. A material according to claim 17 wherein the smectogenic compound has a formula

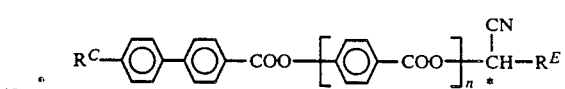

where $R^C$ is n-alkyl containing 1-12 carbon atoms and $R^E$ is C$_{1-12}$ n-alkyl branched alkyl, cyclo alkyl or phenyl alkyl, n being 0 or 1.

20. A material according to claim 19 wherein the smectogenic compound has a formula

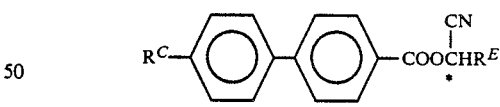

where $R^E$ is branched alkyl.

21. A ferroelectric smectic liquid crystal electro-optic display device containing a liquid crystal material that includes at least one compound of claim 1.

* * * * *